(12) United States Patent
Schakel

(10) Patent No.: US 7,273,607 B2
(45) Date of Patent: Sep. 25, 2007

(54) HEALTH ENHANCEMENT METHOD

(76) Inventor: Karl Walter Schakel, deceased, late of Fort Collins, CO (US); by Karl G. Schakel, legal representative, 1162 Saint Germaine Dr., Fort Collins, CO (US) 80521

( * ) Notice: Subject to any disclaimer, the term of this patent is extended or adjusted under 35 U.S.C. 154(b) by 382 days.

(21) Appl. No.: 10/612,321

(22) Filed: Jul. 1, 2003

(65) Prior Publication Data

US 2004/0052871 A1 Mar. 18, 2004

Related U.S. Application Data

(60) Provisional application No. 60/393,717, filed on Jul. 1, 2002.

(51) Int. Cl.
*A61K 33/00* (2006.01)
*A61K 38/46* (2006.01)
*A61K 35/12* (2006.01)
*A01N 59/00* (2006.01)
*A01N 63/00* (2006.01)
*A01N 65/00* (2006.01)

(52) U.S. Cl. ............... 424/94.6; 424/93.7; 424/94.1; 424/520; 424/600; 424/725; 426/311; 426/390; 426/531; 426/635

(58) Field of Classification Search ............ None
See application file for complete search history.

(56) References Cited

U.S. PATENT DOCUMENTS

| | | | |
|---|---|---|---|
| 4,950,164 A | 8/1990 | Lennon-Thompson et al. | 434/127 |
| 5,044,958 A | 9/1991 | Robertson et al. | 434/127 |
| 5,547,947 A | 8/1996 | Doré et al. | 514/167 |
| 5,807,586 A | 9/1998 | Jackson et al. | 424/630 |
| 5,833,072 A | 11/1998 | Lamblet, Jr. | 206/534 |
| 5,856,317 A | 1/1999 | Doré et al. | 514/167 |
| 5,891,866 A | 4/1999 | Doré et al. | 514/168 |
| 6,039,978 A | 3/2000 | Bangs et al. | 424/489 |
| 6,040,333 A | 3/2000 | Jackson | 514/456 |
| 6,077,828 A | 6/2000 | Abbruzzese et al. | 514/21 |
| 6,090,414 A | 7/2000 | Passwater et al. | 424/702 |
| 6,102,706 A | 8/2000 | Khoo et al. | 434/127 |
| 6,242,435 B1 | 6/2001 | Acakar | 514/168 |

*Primary Examiner*—David M. Naff
*Assistant Examiner*—Deborah K. Ware
(74) *Attorney, Agent, or Firm*—Santangelo Law Offices, P.C.

(57) ABSTRACT

A health enhancement system establishing a health enhancement program through which may be provided a group of natural products, vitamins and minerals, amino acids, herbs and essential oils that may be helpful in aiding the body in fighting the growth of cancers and the progression of other diseases and in reducing the negative side effects of cancer and cancer treatment, and other diseases and their treatment. At least one embodiment of the invention involves a packaging system of the group of natural products, vitamins and minerals, amino acids, herbs and essential oils that the health enhancement system may comprise.

26 Claims, 6 Drawing Sheets

| Beta Caroteno | 1 cápsula |
|---|---|
| Uña de Gato | 1 cápsula |
| Complete | 2 tabletas |
| Dino Bites | 1 tableta |
| Gold | 1 cápsula |
| Omega-3 | 2 cápsulas |
| Osteoguard | 1 tableta |
| Platinum | 2 cápsulas |
| Cartílago de Tiburón | 5 cápsulas |
| Vitamina C | 1 tabletas |
| Vitamina E | 1 cápsulas |

HEALTH ENHANCEMENT METHOD

I. CROSS-REFERENCES TO RELATED APPLICATIONS

This application claim the benefit and priority of U.S. Provisional Application No. 60/393,717, filed Jul. 1, 2002, entitled "System for Improving Results of Treatments and Also for Enhancing an Ability to Resist Certain Types of Disease", hereby incorporated by reference.

II. BACKGROUND

This invention provides a procedure and substances and generally, a health enhancement system which can be used to bolster or improve the body's resistance to certain life threatening conditions such as Cancer, AIDS, Diabetes, Hepatitis, Parkinson's Disease and others. It may be particularly useful when facing a threat or risk of some cancers in humans. The system may establish a health enhancement program through which is provided a group of natural products, vitamins and minerals, aminoacids, herbs and essential oils that may be helpful in aiding the body in fighting the growth of cancers and the progression of other diseases and in reducing the negative side effects of cancer and cancer treatment, and other diseases and their treatment(s). It may also assist in slowing, stopping, or reversing the growth of some cancers in the user. According to one embodiment, the body's ability to achieve a remission of a cancer is believed to be due to its being aided by a unique combination of selected ingredients and dosages. This system may: slow, stop, or reverse the growth of cancerous cells, and/or promotes and strengthen the human bodies own immune defense system against the cancerous cells. Additionally, this system may allow cancer victims to maintain a significant, higher health status, as defined by mobility, weight gain and energy level during treatment and post treatment. In one embodiment the ingredients may themselves be significant. In another embodiment, the amount, timing and frequency in which the products are taken may have a significant impact on the treatment performance. The products may also be presented in a unit dose packaging system that may improve the patient's ability to accurately follow the use methodology prescribed. As should be appreciated, the packaging system may also be applied and used for other administrations as well. In order to track effectiveness and/or assure system processes, a set of medical tests may be required of the patient before and during the course of the treatment. The tests can be collected and analyzed by the administrator or a health professional to aid in obtaining information on the progress of the patient. There may also be further evidence of the efficacy of the products or the system in various cases.

There have been numerous research reports and claim published on the ability of natural products, vitamins and minerals to provide either enhancements or even effective, alternative means for conventional treatments (surgery, chemotherapy and radiation) of some human cancers. Most of this research has focused on the use of one or a limited number of natural products against a particular type of cancer. Often research has been inconclusive with both positive and negative results reported. The present invention provides a new approach to both the products used, the systems followed, and the reporting requirements of a treatment system. It may be applicable in a wide range of treatments; however, it is of particular applicability for a multi-faceted treatment such as proposed to bolster a battle against certain forms of cancer. In one embodiment, the invention may also be used in combination or conjunction with conventional treatments such as surgery, chemotherapy and radiation therapy. This combination may again provide multiple backups and synergies that may provide more effective control than any one treatment or product or therapy. Again, as data is collected (perhaps as part of the inventions data collection system) other preferred embodiments may also be derived.

III. DESCRIPTION OF THE DRAWINGS

IV. SUMMARY OF THE INVENTION

Figure 1:
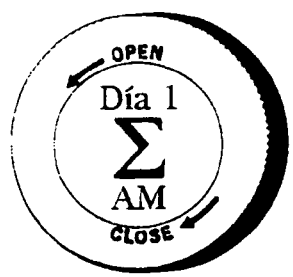
FIG. 1 illustrates a unit dose design according to one embodiment.
Figure 1:
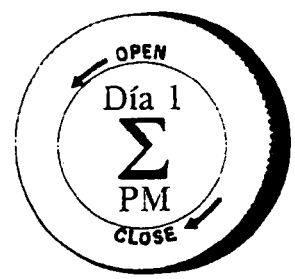
Figure 1:
Figure 1:
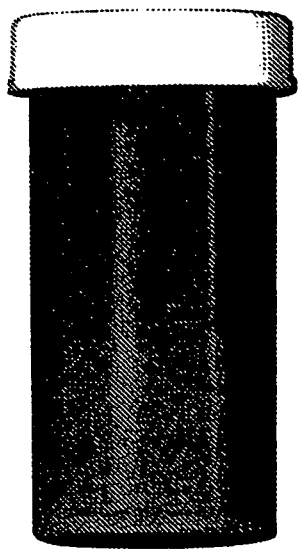
Figure 1:
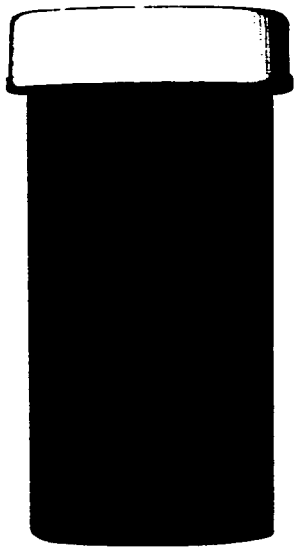
Figure 2:
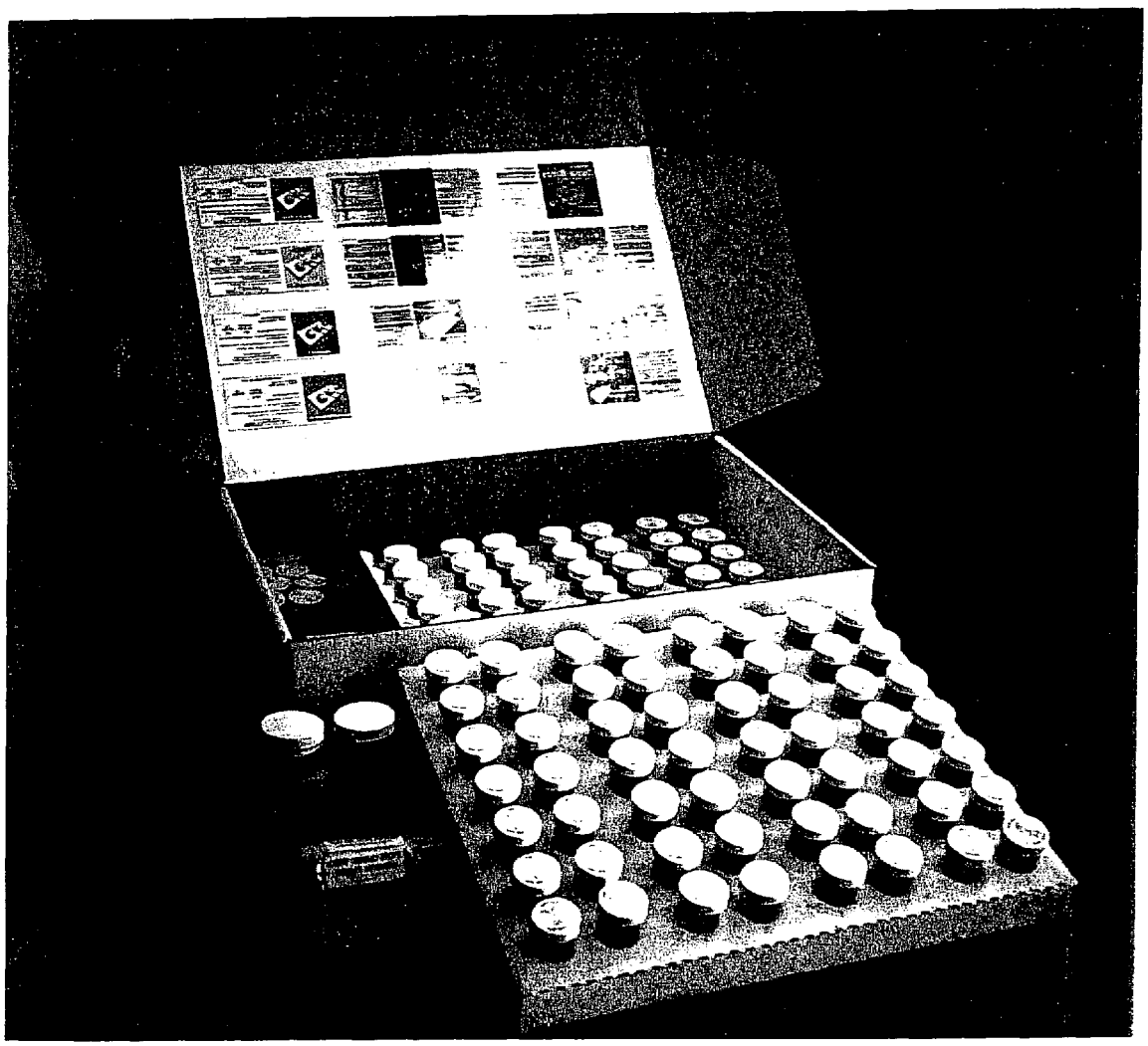
FIGS. 2-4 illustrate one embodiment of the packaging system aspect of the invention.
Figure 3:
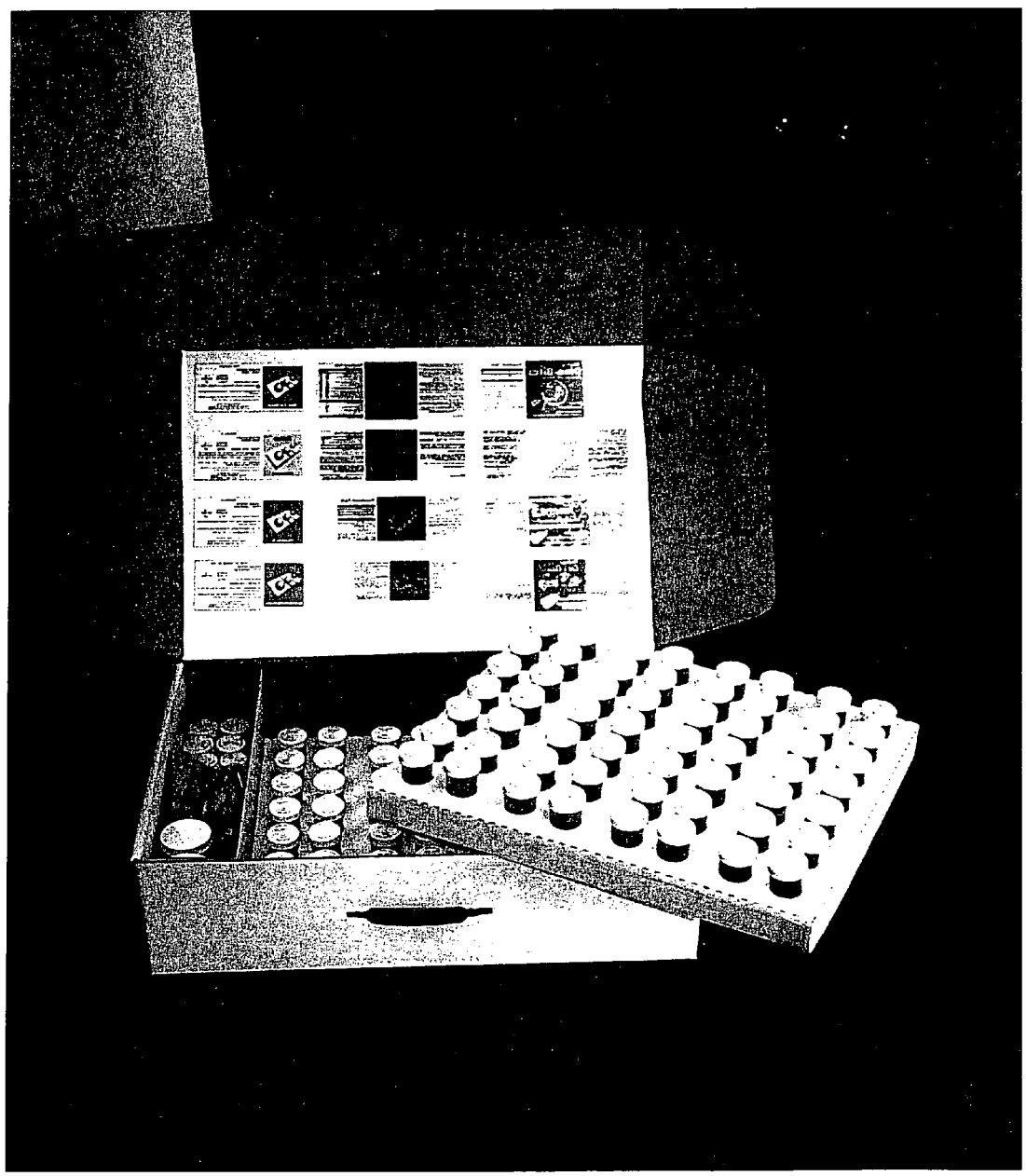
Figure 4:
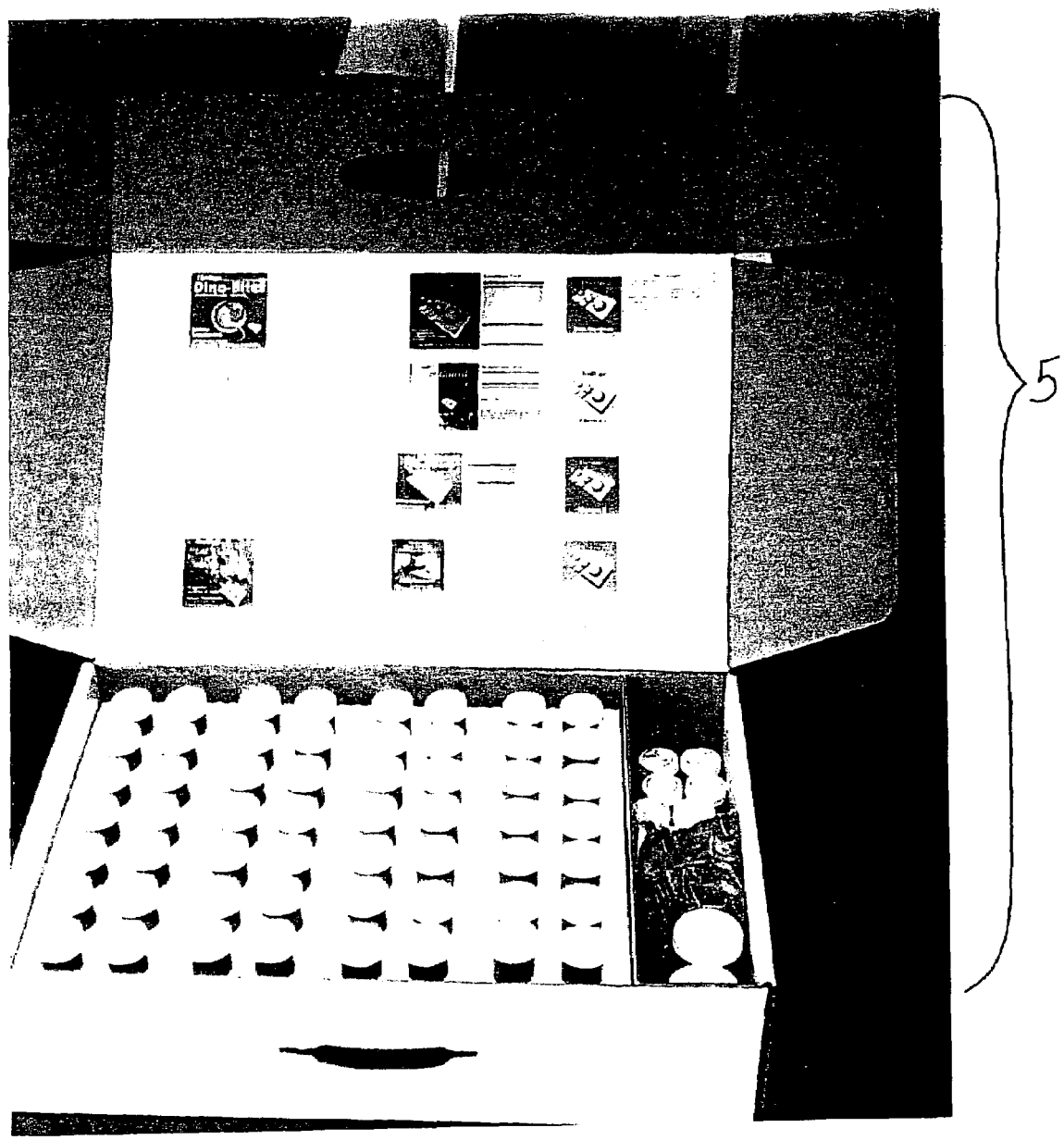
Figure 5:
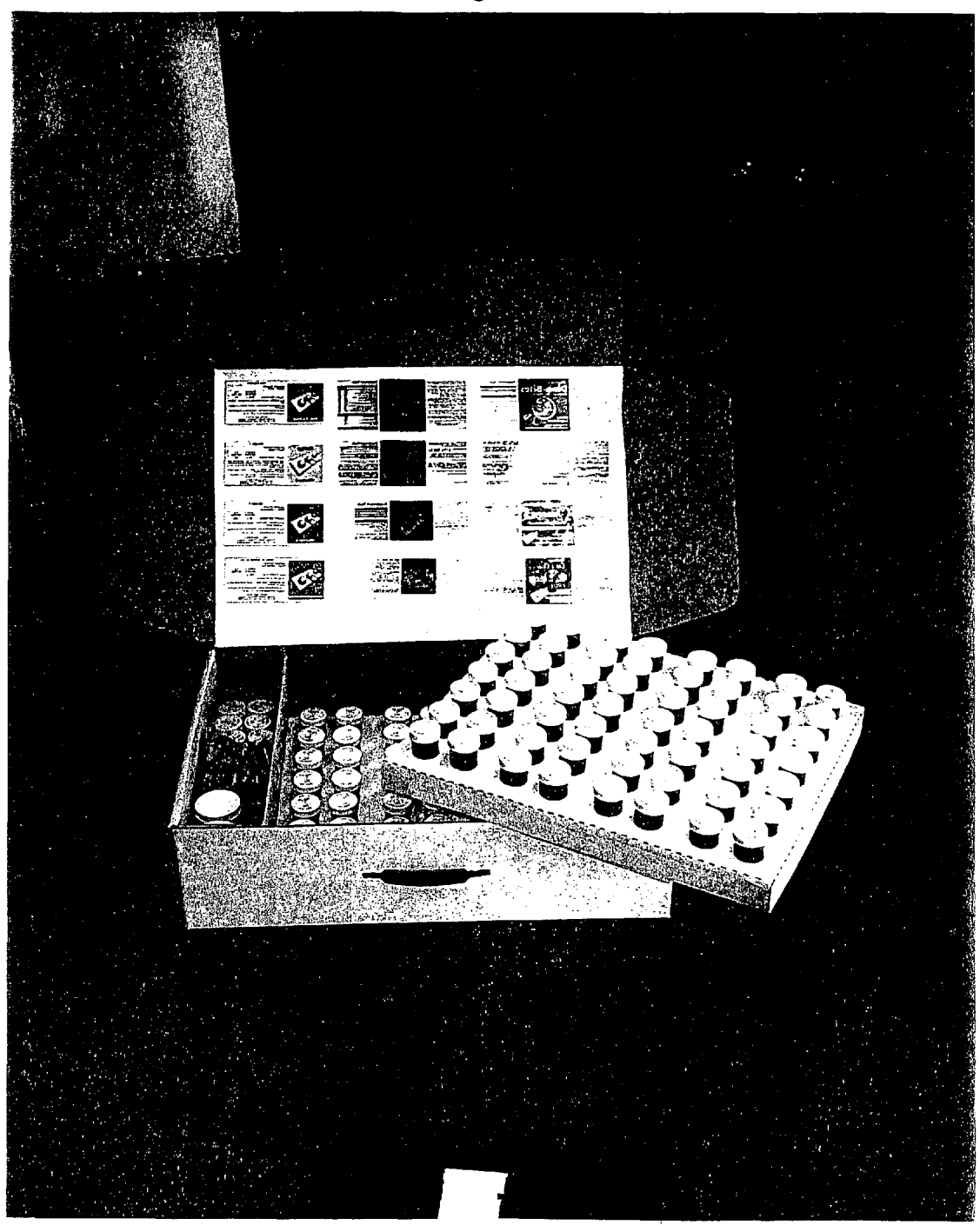
Figure 6:
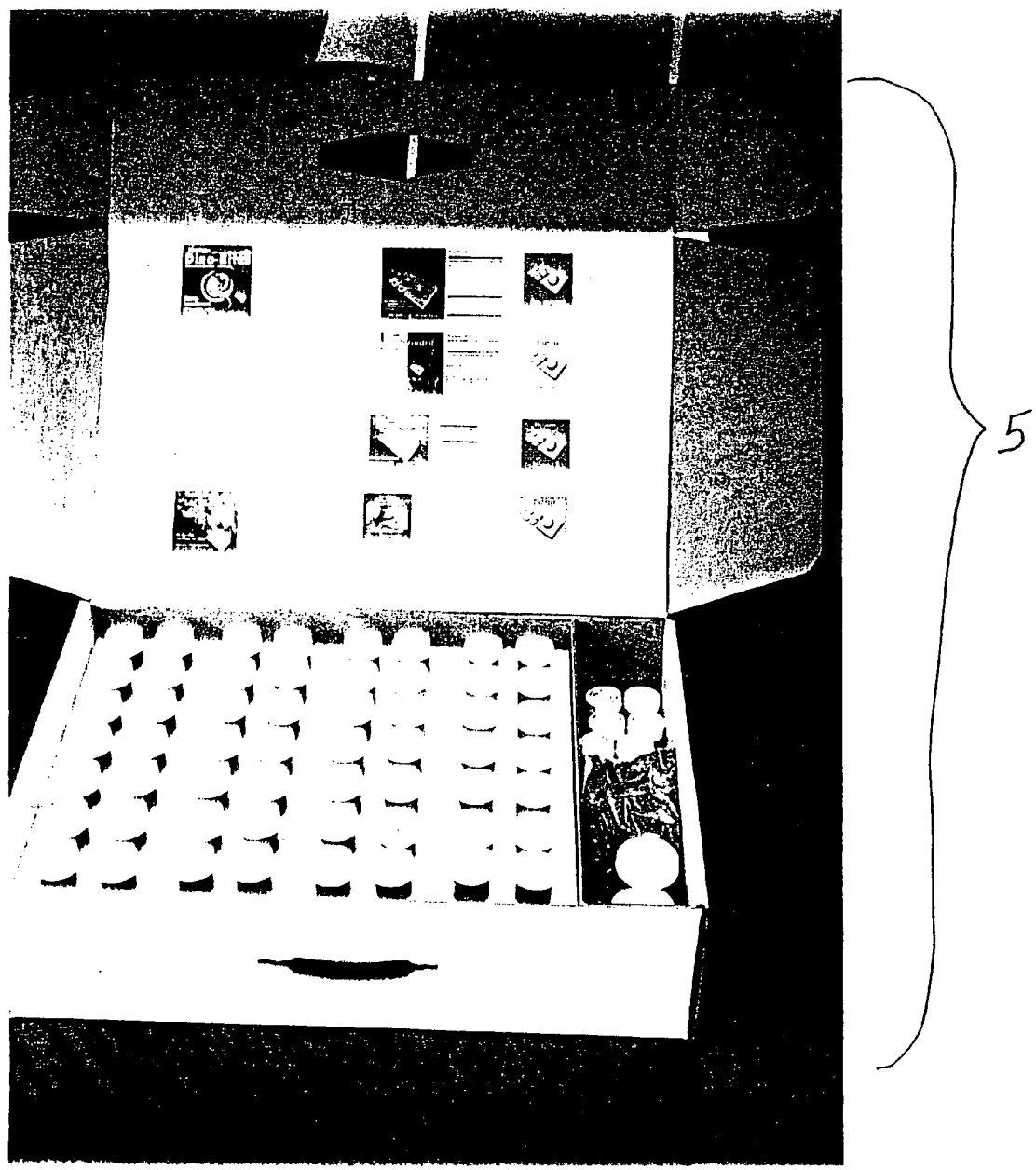

It is a goal of this invention to provide the cancer patient with a complement of natural products, vitamins, minerals, amino acids, herbs and essential oils and other ingredients that may directly attack the cancerous cells, which may strengthen and improve the body's own defense immune system against cancer, or which may otherwise aid a person in a battle against cancer and other diseases. The present invention provides both a formulation of ingredients and nutrients for a patient, a system of use, and a system of administration of such a treatment. It provides for the proper dosage and accurate ordering by a person in order to assure accuracy of such a potentially complex inter-relation of preferably natural substances. In one embodiment, the invention may contain ingredients that have been selected based on their purported ability by themselves to slow or stop the growth of cancerous cells. It may also contain selected levels of vitamins, minerals, and other nutrients that have been determined to enhance the body's natural defense systems.

V. DETAILED DESCRIPTION OF THE PREFERRED EMBODIMENTS

As can be easily understood, the basic concepts of the present invention may be embodied in a variety of ways. It may involve, among other aspects, a set of ingredients, a series of formulations, a grouping of dosages, a packaging system, unit dose system, and even a data collection system in order to accomplish the intended results.

Ingredients:

In one embodiment, the invention's differentiation from other treatments, in part, maybe considered a result of the use of ingredients that when combined provide effects against cancer cells that may fall outside of, or in addition to the logical expectation of any single ingredient. Many natural products, herbs, vitamins and minerals have been tested as potential treatments against cancer. Recently, many researchers have tested single ingredients, or in some cases, combinations of two or three natural products against specific cancer types with mixed results. These mixed results may in part be due to the fact that the mechanisms of some various forms of cancer may not be well understood by current science or at least by the researchers. The mixed results may also be due to some degree by the fact that the researchers may have been primarily focused on finding a single product or ingredient, which is effective against a certain type of cancer. Interrelationships may have been difficult to understand.

In one embodiment, the invention may differ from the single ingredient/specific cancer approach. While the single ingredient/specific cancer approach may provide the most accurate information to the researcher on the mechanisms of cancer cell growth, it may do little for the patient who dies if the treatment is not effective against the type of cancer the patient has. In one embodiment, the invention may be considered as based upon the fact that a combination of ingredients working synergistically may prove to be more effective against cancer than any one ingredient by itself. This approach may result in better long-term success rates for cancer patients than any single ingredient can provide and tests seem to confirm this aspect.

The present invention includes a variety of ingredients which may be ingested in a combined manner in different ways to achieve the intended result. At least one embodiment of the health enhancement system establishes a 60 day health enhancement program, but certainly programs of other lengths (including non-stop during the life of the program participant) should be understood as encompassed by this disclosure.

Each of these ingredients is first discussed separately with a preferred combination also mentioned. However all the various permutations and combinations of the individual ingredients should be understood as encompassed by this disclosure.

The invention may be comprised of two subsets of products that when combined could have the ability to more effectively stop, slow, or even reverse a growth of cancer cells or to more appropriately enhance the body's own processes in such a situation. The first subset includes ingredients that have been previously reported to individually have specific, potentially direct effects on cancerous cells as follows:

Shark Cartilage: may inhibit the growth of blood vessels that feed cancerous tumors. This may cut off the nutrition to the tumor and therefore may not allow the tumor to continue to grow and mutate and to therefore die.

Essiac Tea: a four-herb tea developed by an oncology nurse in 1922, this formula may be excellent for maintaining and healing the liver which is responsible for detoxifying the blood which may be important in fighting cancer. This formulation may contain burdock root (Arcticum lappa), slippery elm (Ulmus fulva), turkey rhubarb (Rheum palmatum), and sheep sorel (Rumex acetosella). It may also itself serve to kill certain cancer cells. It may be prepared and used as set forth in Table 3. It may be important to note that the term essiac tea may refer to the herbal liquid (see Table 3) that may be used to make the prepared beverage upon dilution of the herbal liquid with warm water.

Table 3 lists a preparation procedure and some use options for the essiac tea feature of the invention.

TABLE 3

ESSIAC TEA

Preparation of the 4-Herb Formula

SUPPLIES NEEDED.
Stainless steel or enamel canning pot (size: 2 gallons or 8 liters) with lid. (Do not use aluminum.)
Another large pot to pour hot liquid into while you strain it. This can be Pyrex or stainless steel.
Stainless steel mesh strainer and spoon and ladle (a large soup serving spoon)
16 ounce (⅛ liter) or 32 ounce (¼ liter) amber glass bottles in which to TABLE 3-continued

ESSIAC TEA store your finished product (they should be amber or a dark color, as the formula is light sensitive and will not stay as potent in clear glass bottles)

Preparation Procedure

To make the one gallon recipe, use the four herb-package (approximately ½ cup).
Bring one gallon of water to a boil. Stir in herbs, replace lid and boil for 10 minutes.
Turn off stove, scrape down sides, mix well and allow pot to sit and remain closed for 12 hours.
(This is the steeping and extraction process.)
After 12 or more hours, reheat to almost boiling (about 10 minutes). Let cool for 5 minutes and begin straining process. Strain as many times as you like. A little herb left in the liquid will not hurt it in any way. It is also satisfactory to allow the solids, etc. to settle to the bottom and then skim off the liquid with a soup ladle. Reheat your liquid once again (2 to 3 minutes only). This will kill any bacteria that may have landed in your liquid and help keep it from spoiling.
Using a funnel or a glass measuring cup, put your hot liquid into pre-heated
bottles. You can heat the bottles in the oven at 200 degrees for 5 or 10 minutes. Do not put bottle caps in oven!
Cap, let cool and then put in the refrigerator. This will be good for one month. Label the bottles the day you make the tea and also the day it expires.

Directions for Use

Mix 2 ounces of herbal liquid with two ounces of warm water. Never heat this formula or the hot water in a microwave!
The formula should be taken on an empty stomach to allow for better absorbability. Always take before eating. Wait 15 to 20 minutes before eating.
This formula can be taken 1 to 3 times per day. The herbal formula is non-toxic in proper doses and has a pleasant taste similar to black tea. These herbs do stimulate the body to throw off toxins and, therefore, it is important that you drink plenty of clean water and have regular bowel movements.
For cancer and serious ailments the dosage is 3 times per day for as long as tests indicate the presence of cancer. Then 2 times per day for an additional year. For long term maintenance and gentle detoxification the dosage is 1 time per day.

Flax Oil: this is a source of linolenic and linoleic acids, which may be vital in providing nutrients to the non-cancer cells. These compounds contained in flax may also attack the mutating cells in a manner, which does not significantly affect healthy body cells and may not possess the destructive side effects of conventional chemotherapy.

Omega 3 oil: this is an additional source of linoleic and linolenic acids from certain fish species.

Hydrazine Sulfate: used to treat cachexia, and symptoms associated with chemotherapy, such as loss of hair, nausea, pain, weight loss, and general deterioration of vital organs, the body, and muscles. This may be considered a MAO inhibitor, and may allow the body to tolerate chemotherapy while allowing the organ systems to continue the processing of nutrition.

Cat's Claw: (Una de Gato) potentially a strong anti-oxidant although often used in central and south America for centuries as a general wellness product. It may have alkaloids (vinca alkaloids), which may have anti-tumor properties much like the chemotherapy drugs Vincristine and Vinblastine; only this nutritional product may be largely free of the side effects.

In one embodiment, a goal of this first subset of ingredients may be considered as providing multiple, alternative products that are selected to have some type of anti-cancer cell properties. Since the effects of each of the above ingredients on cell growth of the many different types of cancer may be considered as not totally understood by current science, in a general sense, the invention may be considered as providing multiple backups and synergies that may provide more effective control than any one or two of the products. As more data is collected (potentially as part of the invention's data collection system), other preferred embodiments may be derived. These embodiments may include more ingredients, or fewer, as the results dictate.

The second subset of ingredients can be generally described as natural products, vitamins and minerals that are selected for their positive effects on the body's ability to build and maintain a healthy immune defense system. This subset of ingredients may include the following:

Products sold under the trademark Heritage Complete™ or the like (such as provided by Heritage Health™ Products): A particularly good multiple vitamin and amino acid and mineral product. This may be selected to provide the body the basic building blocks of nutritional components to sustain health during the cancer fight and thereafter their ingredients (To the extent composite products such as this are referenced, all each incorporated by reference herein.), as publicly available.

Products sold under the trademark Dino Bites™ or the like (such as provided by Heritage Health™ Products): a montmorillonite mineral supplement used in concert with the above complete multiple vitamin product to ensure absorption of the vitamins and to provide more than sixty trace minerals.

Vitamin C: (ascorbic acid ester) a necessary building block to provide energy for the Krebs cycle as well as an excellent anti-oxidant.

Vitamin A: (beta-carotene) a strong antioxidant that deals directly with and destroys free radicals produced from use of radiation and chemotherapy.

Vitamin E: (d-alpha-tocopherol) another strong antioxidant as well as a facilitator of fat-soluble vitamins. Also responsible for regulation of blood flow with regard to prevention of blood clots.

Products sold under the trademark Heritage Osteoguard™ or the like (such as provided by Heritage Health™ Products): a hydroxyadpatite calcium and magnesium supplement that may ensure the patient has bone strength. Chemotherapy, without a calcium supplement, can remove the required calcium from the bones of the patient, ultimately causing weakness and a general sense of malaise.

Products sold under the trademark Heritage Platinum™: (oligomeric proanthocyanidins) or the like (such as provided by Heritage Health™ Products) may provide strengthened immune function, stimulates T-4 killer cell production as well as white blood cell production, which may be critical to attacking mutated cancer cells. This may serve as an overall nutritional supplement for the immune system.

Products sold under the trademark Heritage Gold™ or the like (such as provided by Heritage Health™ Products): a digestive enzyme product, which is critical in the breakdown of food. Often cancer patients are intolerant to retention of food; this may serve to break down the oils that the health enhancement system may comprise.

In one embodiment, a goal of this second subset of ingredients may be to provide the body with important nutrients and vitamins that may allow the body's natural immune defense system to complement the first subset of ingredients. This may also provide far more effective control of the cancer cells, and may maintain better health in the patient. Because the effects of each of the above ingredients on the body's natural immune defense system may also be considered as not totally understood by current science from some perspectives, the invention may again provide multiple backups and synergies that may provide more effective control than any one product. Again, as data is collected (perhaps as part of the invention's data collection system), other preferred embodiments may be derived. These embodiments may include more ingredients, or fewer, or some additional ones, as results dictate.

In one preferred embodiment of the health enhancement system, the dosage and/or timing of the ingredients may be considered important. One such system of dosages and timing is shown in Tables 1 and 2. Importantly, it should be understood that these dosages and/or timings of the listed ingredients are elements of a health enhancement system establishing a health enhancement program that, in Tables 1 and 2, is a preferred embodiment as currently understood. Other dosages and timings may prove to be appropriate and may produce satisfactory results and to the extent the ingredients are disclosed herein, all permutations and combinations—even of each elements' subelements—should be understood as encompassed by this disclosure. Specifically, elimination of one or more of the ingredients from the system presented in Tables 1 and 2, or alteration of the dosage and/or timing of the ingredients presented in Tables 1 and 2 is to be understood as encompassed by this disclosure. As data is collected (perhaps as part of the invention's data collection system), other preferred embodiments may be derived. These embodiments may include higher or lower dosages of each of the ingredients, separately or in total. It may be important to understand that a daily portion of any ingredient may be in two or more smaller portions (e.g., one of which is for ingestion in the morning and the other, in the evening).

Tables 1 and 2 list some of the possible systems of dosages and timings for some embodiments.

TABLE 1

| Products and Dosage |
|---|
| 1. Flax Oil - 2 capsules (1,000 mg each) each morning and evening. |
| 2. Heritage Omega - 3 Oil 1 2 capsules (1,000 mg each) each morning and evening. |
| 3. Shark Cartilage - 5 capsules (250 mg each) each morning and evening. |
| 4. Heritage Dino Bites - (montmorillinite minerals) 1 tablet (300 mg) each morning and evening. |
| 5. Vitamin C - 2 tablets (500 mg each) each morning and evening. |
| 6. Beta Carotene (Vitamin A) - 1 capsule (25,000 IU) every two days. |
| 7. Heritage Complete - 2 tablets each morning and evening. Each tablet consists of multivitamins and minerals:: |

| | |
|---|---|
| Vitamin A | 1,666 IU |
| Vitamin C | 100 mg |
| Vitamin D | 66 IU |
| Vitamin E | 33 IU |
| Vitamin K | 13 mcg |
| Thiamin | 2.5 mg |
| Riboflavin | 2.8 mg |
| Niacin | 17 mg |
| Vitamin B6 | 3.3 mg |
| Folic Acid | 67 mcg |
| Vitamin B12 | 10 mcg |
| Biotin | 50 mcg |
| Pantothenic Acid | 10 mg |
| Calcium proteinate | 17 mg |
| Iodine | 25 mcg |
| Magnesium | 17 mg |

TABLE 1-continued

Products and Dosage

| | | |
|---|---|---|
| | Zinc | 2.5 mg |
| | Selenium | 12 mcg |
| | Copper proteinate | 0.33 mg |
| | Manganese | 1.7 mg |
| | Chromium | 34 mcg |
| | Molybdenum | 17 mcg |
| | Potassium | 17 mg |
| | Garlic Cloves | 83 mg |
| | Choline | 34 mg |
| | Inositol | 17 mg |
| | PABA | 17 mg |
| | Boron | 0.5 mg |
| | Octosanol | 0.5 mg |
| | Silicon | 0.17 mg |
| | Vanadium | 17 mcg |
| | Blend: Chlorella, Korean Ginseng, Lemon bioflavenoids, Papain, Rose Hips, Rutin, Coenzyme Q 10. | |
| 8. | Heritage Osteoguard - 1 tablet each morning and evening. Each tablet contains: | |
| | Vitamin D | 10 IU |
| | Hydroxyadpatite and citrate | 250 mg |
| | Magnesium (as citrate) | 100 mg |
| 9. | Heritage Platinum - 2 capsules each morning and evening. Each capsule contains: | |
| | Pine Bark Extract | 10 mg |
| | Grape Seed Extract | 40 mg |
| | Blend of citrus bioflavenoids, Rutin, Quercetin | |
| 10. | Heritage Cat's Claw 11 capsule ( 600 mg) each morning and evening | |
| 11. | Heritage Gold - 1 capsule each morning and evening. Each capsule contains Pancreatin, Lactase, Lipase, Amylase, Catalase, Chrymotrypsin, Trypsin, Cellulase, Zinc Gluconate. | |
| 12. | Vitamin E - 1 softgel (400 IU) each morning and evening. | |
| 13. | Essiac Tea - Drink 2 ounces of tea 3 times daily at least 20 minutes prior to eating. | |
| 14. | Hydrazine Sulfate - 60 mg tablets. | |
| | A. One tablet daily for first three days. | |
| | B. Two tablets daily for days 4, 5, and 6. | |
| | C. Three tablets daily for the following 46 days. | |
| | D. No tablets for 7 days. | |

TABLE 2

Products and Dosage

| | | |
|---|---|---|
| 1. | Flax Oil - 2 capsules (1,000 mg each) each morning and evening. | |
| 2. | Heritage Omega - 3 Oil - 2 capsules (1,000 mg each) each morning and evening. | |
| 3. | Shark Cartilage - 10 capsules (250 mg each) each morning and evening. | |
| 4. | Heritage Dino Bites - (montmorillinite minerals) 1 tablet (300 mg) each morning and evening. | |
| 5. | Vitamin C - 2 tablets (500 mg each) each morning and evening. | |
| 6. | Beta Carotene (Vitamin A) - 1 capsule (10,000 IU) every morning. | |
| 7. | Heritage Complete - 3 tablets each morning and evening. Each tablet consists of multivitamins and minerals:: | |
| | Vitamin A | 1,666 IU |
| | Vitamin C | 100 mg |
| | Vitamin D | 66 IU |
| | Vitamin E | 33 IU |
| | Vitamin K | 13 mcg |
| | Thiamin | 2.5 mg |
| | Riboflavin | 2.8 mg |
| | Niacin | 17 mg |
| | Vitamin B6 | 3.3 mg |
| | Folic Acid | 67 mcg |
| | Vitamin B12 | 10 mcg |
| | Biotin | 50 mcg |
| | Pantothenic Acid | 10 mg |
| | Calcium proteinate | 17 mg |
| | Iodine | 25 mcg |
| | Magnesium | 17 mg |
| | Zinc | 2.5 mg |
| | Selenium | 12 mcg |
| | Copper proteinate | 0.33 mg |
| | Manganese | 1.7 mg |
| | Chromium | 34 mcg |
| | Molybdenum | 17 mcg |
| | Potassium | 17 mg |
| | Garlic Cloves | 83 mg |
| | Choline | 34 mg |
| | Inositol | 17 mg |
| | PABA | 17 mg |
| | Boron | 0.5 mg |
| | Octosanol | 0.5 mg |
| | Silicon | 0.17 mg |
| | Vanadium | 17 mcg |
| | Blend: Chlorella, Korean Ginseng, Lemon bioflavenoids, Papain, Rose Hips, Rutin, Coenzyme Q 10. | |
| 8. | Heritage Osteoguard - 1 tablet each morning and evening. Each tablet contains: | |
| | Vitamin D | 10 IU |
| | Hydroxyadpatite and citrate | 250 mg |
| | Magnesium (as citrate) | 100 mg |
| 9. | Heritage Platinum - 2 capsules each morning and evening. Each capsule contains: | |
| | Pine Bark Extract | 10 mg |
| | Grape Seed Extract | 40 mg |
| | Blend of citrus bioflavenoids, Rutin, Quercetin | |
| 10. | Heritage Cat's Claw - 1 capsule (600 mg) each morning and evening | |
| 11. | Heritage Gold - 1 capsule each morning and evening. Each capsule contains Pancreatin, Lactase, Lipase, Amylase, Catalase, Chrymotrypsin, Trypsin, Cellulase, Zinc Gluconate. | |
| 12. | Vitamin E - 1 softgel (400 IU) each morning and evening. | |
| 13. | Essiac Tea - Drink 2 ounces of tea 3 times daily at least 20 minutes prior to eating. | |

In another embodiment, the user may also be encouraged to modify their diet in two main ways. First, to greatly reduce fat content to less than 25% of total daily caloric intake, especially of saturated fats. Second, to add daily portions of cruciferous vegetables at every meal possible. In combination with other aspects of the invention, the multiple synergies and backups may provide more effective control than any one treatment or therapy.

Unit Dose Packaging System

As shown in FIG. 1 the invention may be presented to a user in a unit dose design. The appropriate dose of each ingredient may even be packaged for sequential use, such as once each morning and evening by the user. This design may increase the accuracy and timing of the dosing by the patient, and may increase the efficacy. Given the need to maintain a consistent level of each ingredient in the patient, one goal of this feature of the invention may be to make a complex administration system easier for the patient to take the proper dosage at the correct times.

In one preferred embodiment, the proper dosage of each of the ingredients may be included as part of a package of ingredients (5) that comprises daily portions of a multi-day supply (such as a one week or seven day supply, e.g.) usable in a health enhancement program for use by the patient at the preferred times, e.g., once each morning and evening. However, other dosages and timings may be appropriate to give the intended result. In this regard, combinations using morning and evening administrations as well as three times per day, four times per day, and even once per day (as but a few examples) should be understood as encompassed by this disclosure as each may be appropriate in a given context. In at least one embodiment, the ingredients are relationally coordinated in that the type and/or dosage and/or timing is selected to cause a health enhancing effect. Based on the information gathered through the use of the data collection system, dosages and timings of each ingredient may even be altered, increased or decreased to maximize the effectiveness. A rapid feedback process may even be implemented to optimize effectiveness for each user.

Data Collection System

As a way to assure or perhaps enhance efficacy, and perhaps also as a way to encourage usage and even track the effectiveness of the invention, a data collection system may be implemented. In one embodiment, certain personal, usage, and/or medical records of the patient/customer may be collected. One goal of this system may be to insure that information is gathered which may be necessary to allow the effectiveness of the invention to be demonstrated, and which may be useful to consider adjustments made to the ingredients, timing, dosages and packaging system for maximum effectiveness, and which may be useful for marketing purposes. Additionally, this system may serve to encourage the customer/patient to be under the care of a medical professional which may not only assure optimal care, but it may also enhance the perceptions by the patient and thereby enhance the system's effectiveness.

In a preferred embodiment, the data collection system may be designed to require that each patient/customer of a kit produce certain medical records at the time of purchase. These records may include diagnosis, prognosis, list of current medicines, treatment and medical history and other appropriate tests such as blood tests etc. Periodically, the patient/customer may also be required to update these medical records, such as on a monthly, weekly, bi-weekly, or even bimonthly basis, but at least at the time of each subsequent sale, in order to track the progress of their disease and perhaps even determine the propriety of any additional purchases.

It may be useful to note that the invention and its formulation appear to have produced what may be considered by some to be spectacular results. Although these results may be considered as only representing a limited test basis, they are significant to those having used the system (including an inventor hereof relative to an advanced case of one of the most deadly forms of cancer, multiple myeloma or bone cancer). Through the use of data collected under one embodiment, further analysis of the results may also be accomplished.

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should further be understood to support and encompass descriptions and claim of all the various embodiments, systems, techniques, methods, devices, and applications with any number of the disclosed elements, with each element alone, and also with any and all various permutations and combinations of all elements in this or any subsequent application.

As can be easily understood from the foregoing, the basic concepts of the present invention may be embodied in a variety of ways. The invention may be considered as involving a combination of ingredients, formulations of the ingredients, timing and dosages of ingredients, a unit dose system, a health enhancement system that establishes a health enhancement program, a packaging system and the like as well as all combinations and permutations of these to improve the efficacy of treatments. It may also include a data collection system to accomplish the desired result of slowing or stopping the growth of cancer cells or the disease in humans and other purposes. While some ingredients, formulations, dosing, methods of packaging and a system of data collection are disclosed, it should be understood that these not only accomplish certain results but also can be varied in a number of ways. Importantly, as to all of the foregoing each and all of these facets should be understood to be encompassed by this disclosure.

It involves both health enhancement techniques as well as devices to accomplish the appropriate and desired enhancement or improvement of health. In this application, the health enhancement techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this non-provisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claim may not only be included for the device described, but also method or process claim may be included to address the functions the invention and each element performs. Neither the description nor the terminology is intended to limit the scope of the claim included in this patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods and/or processes and/or systems and the like are encompassed by this disclosure, in addition to certain narrower embodiments. With this understanding, the reader should be aware that this disclosure is to be understood to support the claim in this patent application. It should be understood that the applicant may later seek examination of, e.g., even broader claim deemed within the applicant's right.

Further, each of the various elements of the invention and claim may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "package" should be understood to encompass disclosure of the act of "packaging"—whether explicitly discussed or not—and, conversely, were there effectively disclosure of the act of "packaging", such a disclosure should be understood to encompass disclosure of a "package" and even a "means for packaging". Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the health enhancement systems as herein disclosed and described, ii) the related methods disclosed and described, iii) similar, equivalent, and even implicit variations of each of these systems and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claim or concepts presented.

With regard to claim whether now or later presented for examination, it should be understood that for practical reasons and so as to avoid great expansion of the examination burden, the applicant may at any time present only initial claim or perhaps only initial claim with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claim at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claim herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claim set forth at any time are hereby incorporated by reference as part of this description of the invention, and the applicant expressly reserves the right to use all of or a portion of such incorporated content of such claim as additional description to support any of or all of the claim or any element or component thereof, and the applicant further expressly reserves the right to move any portion of or all of the incorporated content of such claim or any element or component thereof from the description into the claim or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method for health enhancement comprising the steps of ingesting:

two thousand mgs. of flax oil twice daily;
two thousand mgs. omega-3 oil twice daily;
2500 mgs. shark cartilage twice daily;
300 mgs. montmorillinite minerals twice daily;
one thousand mgs. vitamin C twice daily;
10,000 IU beta carotene daily;
three tablets twice daily, each including: 1,666 IU Vitamin A, 100 mg Vitamin C, 66 IU Vitamin D, 33 IU Vitamin E, 13 mcg Vitamin K, 2.5 mg thiamin, 2.8 mg riboflavin, 17 mg niacin, 3.3 mg Vitamin B6, 67 mcg folic acid, 10 mcg Vitamin B12, 50 mcg biotin, 10 mg pantothenic acid, 17 mg calcium proteinate, 25 mcg iodine, 17 mg magnesium, 2.5 mg zinc, 12 mcg selenium, 0.33 mg copper proteinate, 1.7 mg manganese, 34 mcg chromium, 17 mcg molybdenum, 17 mg potassium, 83 mg garlic cloves, 34 mg choline, 17 mg inositol, 17 mg PABA, 0.5 mg boron, 0.5 mg octosanol, 0.17 mg silicon, 17 mcg vanadium, and a blend of: chlorella, korean ginseng, lemon bioflavenoids, papain, rose hips, rutin, and coenzyme Q10;

one tablet twice daily, each including: 10 IU Vitamin D, 100 mg magnesium as citrate, 250 mg hydroxyadpatite and citrate;

two capsules twice daily, each including: 10 mg pine bark extract, 40 mg grape seed extract and a blend of citrus bioflavenoids, rutin and quercetin;

600 mgs. twice daily, each including:

one capsule twice daily, each including: pancreatin, lactase, lipase, amylase, catalase, chrymortypsin, trypsin, cellulase, and zinc gluconate;

an additional 400 IU vitamin E twice daily; and two ounces essiac tea three times daily.

2. A method for health enhancement as described in claim 1 wherein said step of ingesting two ounces essiac tea three times daily comprises the step of ingesting two ounces of essiac tea three times daily at least 20 minutes prior to eating.

3. A method for health enhancement as described in claim 1 wherein twice daily comprises each morning and evening.

4. A method for health enhancement as described in claim 1 wherein said step of ingesting 10,000 IU beta carotene daily comprises the step of ingesting 10,000 IU beta carotene every morning.

5. A method for health enhancement as described in claim 1 further comprising the step of ingesting fat in a daily caloric amount that is no more than 25% total daily caloric intake.

6. A method for health enhancement as described in claim 1 further comprising the step of ingesting cruciferous vegetables daily.

7. A method for health enhancement as described in claim 1 wherein said health enhancement method comprises a cancer treatment method.

8. A method for health enhancement comprising the steps of ingesting:

four thousand mgs. of flax oil daily;

four thousand mgs. omega-3 oil daily;

5000 mgs. shark cartilage daily;

600 mgs. montmorillinite minerals daily;

two thousand mgs. vitamin C daily;

10,000 IU beta carotene daily;

six tablets daily, each including: 1,666 IU Vitamin A, 100 mg Vitamin C, 66 IU Vitamin D, 33 IU Vitamin E, 13 mcg Vitamin K, 2.5 mg thiamin, 2.8 mg riboflavin, 17 mg niacin, 3.3 mg Vitamin B6, 67 mcg folic acid, 10 mcg Vitamin B12, 50 mcg biotin, 10 mg pantothenic acid, 17 mg calcium proteinate, 25 mcg iodine, 17 mg magnesium, 2.5 mg zinc, 12 mcg selenium, 0.33 mg copper proteinate, 1.7 mg manganese, 34 mcg chromium, 17 mcg molybdenum, 17 mg potassium, 83 mg garlic cloves, 34 mg choline, 17 mg inositol, 17 mg PABA, 0.5 mg boron, 0.5 mg octosanol, 0.17 mg silicon, 17 mcg vanadium, and a blend of: chlorella, korean ginseng, lemon bioflavenoids, papain, rose hips, rutin, and coenzyme Q10;

two tablets daily, each including: 10 IU Vitamin D, 100 mg magnesium as citrate, 250 mg hydroxyadpatite and citrate;

four capsules daily, each including: 10 mg pine bark extract, 40 mg grape seed extract and a blend of citrus bioflavenoids, rutin and quercetin;

1200 mgs. daily, each including:

two capsules daily, each including: pancreatin, lactase, lipase, amylase, catalase, chrymortypsin, trypsin, cellulase, and zinc gluconate;

an additional 800 IU vitamin E daily; and six ounces essiac tea daily.

9. A method for health enhancement as described in claim 8 wherein said step of ingesting six ounces essiac tea daily comprises the step of ingesting two ounces essiac tea three times daily at least 20 minutes prior to eating.

10. A method for health enhancement as described in claim 8 further comprising the step of ingesting fat in a daily caloric amount that is no more than 25% total daily caloric intake.

11. A method for health enhancement as described in claim 8 further comprising the step of ingesting cruciferous vegetables daily.

12. A method for health enhancement as described in claim 8 wherein said method comprises a cancer treatment method.

13. A method for health enhancement comprising the steps of ingesting:

two thousand mgs. of flax oil twice daily;

two thousand mgs. omega-3 oil twice daily;

1250 mgs. shark cartilage twice daily;

300 mgs. montmorillinite minerals twice daily;

one thousand mgs. vitamin C twice daily;

25,000 IU beta carotene every two days;

two tablets twice daily, each including: 1,666 IU Vitamin A, 100 mg Vitamin C, 66 IU Vitamin D, 33 IU Vitamin E, 13 mcg Vitamin K, 2.5 mg thiamin, 2.8 mg riboflavin, 17 mg niacin, 3.3 mg Vitamin B6, 67 mcg folic acid, 10 mcg Vitamin B12, 50 mcg biotin, 10 mg pantothenic acid, 17 mg calcium proteinate, 25 mcg iodine, 17 mg magnesium, 2.5 mg zinc, 12 mcg selenium, 0.33 mg copper proteinate, 1.7 mg manganese, 34 mcg chromium, 17 mcg molybdenum, 17 mg potassium, 83 mg garlic cloves, 34 mg choline, 17 mg inositol, 17 mg PABA, 0.5 mg boron, 0,5 mg octosanol, 0.17 mg silicon, 17 mcg vanadium, and a blend of: chlorella, korean ginseng, lemon bioflavenoids, papain, rose hips, rutin, and coenzyme Q10;

one tablet twice daily, each including: 10 IU Vitamin D, 100 mg magnesium as citrate, 250 mg hydroxyadpatite and citrate;

two capsules twice daily, each including: 10 mg pine bark extract, 40 mg grape seed extract and a blend of citrus bioflavenoids, rutin and quercetin;

600 mgs. twice daily of cat's claw;

one capsule twice daily, each including: pancreatin, lactase, lipase, amylase, catalase, chrymortypsin, trypsin, cellulase, and zinc gluconate;

an additional 400 IU vitamin E twice daily, two ounces essiac tea three times daily; and hydrazine sulfate according to a prescribed hydrazine sulfate schedule, wherein said hydrazine sulfate schedule comprises 60 mg. hydrazine sulfate daily for the first three days of use of said method; 120 mgs. hydrazine sulfate daily for days 4, 5 and 6 of use of said method; and 180 mgs. hydrazine sulfate daily for days 7 through 52 of use of said method.

14. A method for health enhancement as described in claim 13 further comprising the step of refraining from ingesting hydrazine sulfate for days 53 through 60 of use of said method.

15. A method for health enhancement as described in claim 13 wherein twice daily comprises each morning and evening.

16. A method for health enhancement as described in claim 13 or 15 wherein said step of ingesting two ounces essiac tea three times daily comprises the step of ingesting two ounces of essiac tea three times daily at least 20 minutes prior to eating.

17. A method for health enhancement as described in claim 13 further comprising the step of ingesting fat in a daily caloric amount that is no more than 25% total daily caloric intake.

18. A method for health enhancement as described in claim 13 further comprising the step of ingesting cruciferous vegetables daily.

19. A method for health enhancement as described in claim 13 wherein said method comprises a cancer treatment method.

20. A method for health enhancement comprising the steps of ingesting:

four thousand mgs. of flax oil daily;

four thousand mgs. omega-3 oil daily;

1250 mgs. shark cartilage daily;

600 mgs. montmorillinite minerals daily;

two thousand mgs. vitamin C daily;

25,000 IU beta carotene every two days;

four tablets daily, each including: 1,666 IU Vitamin A, 100 mg Vitamin C, 66 IU Vitamin D, 33 IU Vitamin E, 13 mcg Vitamin K, 2.5 mg thiamin, 2.8 mg riboflavin, 17 mg niacin, 3.3 mg Vitamin B6, 67 mcg folic acid, 10 mcg Vitamin B12, 50 mcg biotin, 10 mg pantothenic acid, 17 mg calcium proteinate, 25 mcg iodine, 17 mg magnesium, 2.5 mg zinc, 12 mcg selenium, 0.33 mg copper proteinate, 1.7 mg manganese, 34 mcg chromium, 17 mcg molybdenum, 17 mg potassium, 83 mg garlic cloves, 34 mg choline, 17 mg inositol, 17 mg PABA, 0.5 mg boron, 0.5 mg octosanol, 0.17 mg silicon, 17 mcg vanadium, and a blend of: chlorella, korean ginseng, lemon bioflavenoids, papain, rose hips, rutin, and coenzyme Q10;

two tablets daily, each including: 10 IU Vitamin D, 100 mg magnesium as citrate, 250 mg hydroxyadpatite and citrate;

four capsules daily, each including: 10 mg pine bark extract, 40 mg grape seed extract and a blend of citrus bioflavenoids, rutin and quercetin;

1200 mgs. Cat's Claw daily;

two capsules daily, each including: pancreatin, lactase, lipase, amylase, catalase, chrymortypsin, trypsin, cellulase, and zinc gluconate;

an additional 800 IU vitamin E daily;

six ounces essiac tea daily; and hydrazine sulfate.

21. A method for health enhancement as described in claim 1 wherein said step of ingesting hydrazine sulfate comprises the step of ingesting hydrazine sulfate according to a prescribed hydrazine sulfate schedule that comprises 60 mgs. hydrazine sulfate daily for the first 3 days of use of said method; 120 mgs. hydrazine sulfate daily for days 4, 5 and 6 of use of said method; and 180 mgs. hydrazine sulfate daily for days 7 through 52 of use of said method.

22. A meted for health enhancement as described in claim 21 further comprising the step of refraining from ingesting hydrazine sulfate for days 53 through 60 of use of said method.

23. A method for health enhancement as described in claim 1, wherein said step of ingesting six ounces essiac tea daily comprises the step of ingesting two ounces of essiac tea three times daily at least 20 minutes prior to eating.

24. A method for health enhancement as described in claim 1 further comprising the step of ingesting fat in a daily caloric amount that is no more than 25% total daily caloric intake.

25. A method for health enhancement as described in claim 1 further comprising the step of ingesting cruciferous vegetables daily.

26. A method for health enhancement as described in claim 1 wherein said method comprises a cancer treatment method.

* * * * *